United States Patent
Apel et al.

(10) Patent No.: US 7,947,180 B2
(45) Date of Patent: May 24, 2011

(54) METHOD FOR THE AIR BUBBLE-FREE FILING OF THE BLOOD-CONTAINING END OF A HEMODIALYZER WITH A PHYSIOLOGICAL ELECTROLYTE SOLUTION

(75) Inventors: Joern Apel, Grosshansdorf (DE); Max Fischer, Frankfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 628 days.

(21) Appl. No.: 11/920,647

(22) PCT Filed: May 15, 2006

(86) PCT No.: PCT/EP2006/004565
§ 371 (c)(1),
(2), (4) Date: Apr. 9, 2008

(87) PCT Pub. No.: WO2006/122737
PCT Pub. Date: Nov. 23, 2006

(65) Prior Publication Data
US 2009/0230036 A1  Sep. 17, 2009

(30) Foreign Application Priority Data
May 17, 2005  (DE) .......................... 10 2005 022 545

(51) Int. Cl.
*B01D 61/32* (2006.01)
*B01D 61/30* (2006.01)
*B01D 61/28* (2006.01)

(52) U.S. Cl. .............. 210/645; 210/85; 210/86; 210/90; 210/97; 210/104; 210/120; 210/134; 210/136; 210/143; 210/188; 210/252; 210/258; 210/436; 210/472; 210/644; 210/767

(58) Field of Classification Search .................. 210/644, 210/645, 767, 85, 86, 90, 97, 104, 120, 134, 210/136, 143, 188, 252, 258, 436, 472
See application file for complete search history.

(56) References Cited

U.S. PATENT DOCUMENTS

| 5,228,889 | A | | 7/1993 | Cortial et al. |
| 5,259,961 | A | | 11/1993 | Eigendorf |
| 5,591,344 | A | * | 1/1997 | Kenley et al. ................. 210/636 |
| 5,849,065 | A | | 12/1998 | Wojke |

(Continued)

FOREIGN PATENT DOCUMENTS

DE   34 18 434 A1   11/1985

(Continued)

OTHER PUBLICATIONS

English translation Japanese Patent Application No. 3068371.*

(Continued)

*Primary Examiner* — John Kim
(74) *Attorney, Agent, or Firm* — Jacobson Holman PLLC

(57) ABSTRACT

A method and apparatus for the air-free filling of the blood side of a hemodialysis apparatus with a physiological electrolyte solution and for the venting of the blood side of a hemodialysis apparatus during operation includes using a chamber in a blood-removing line system. The blood-removing line system, including the chamber arranged therein, is filled with a physiological electrolyte solution, with a valve arranged above the chamber and connected thereto being opened to fill the chamber completely with the physiological electrolyte solution until it comes into contact with a hydrophobic filter arranged above the valve.

18 Claims, 1 Drawing Sheet

U.S. PATENT DOCUMENTS

| | | |
|---|---|---|
| 5,882,516 A | 3/1999 | Gross et al. |
| 2002/0007137 A1 | 1/2002 | Utterberg et al. |
| 2002/0017489 A1 | 2/2002 | Utterberg |
| 2003/0135152 A1 | 7/2003 | Kollar et al. |
| 2004/0084371 A1 | 5/2004 | Kellam et al. |
| 2004/0228760 A1 | 11/2004 | Stringer et al. |
| 2005/0040110 A1 | 2/2005 | Felding |

FOREIGN PATENT DOCUMENTS

| | | |
|---|---|---|
| DE | 196 07 162 A1 | 9/1997 |
| DE | 100 11 208 C1 | 9/2001 |
| EP | 0 161 686 A2 | 11/1985 |
| EP | 0 560 368 A2 | 9/1993 |
| JP | 61 50564 A | 3/1986 |
| JP | 3 068371 | 3/1991 |
| JP | 6 014964 B | 3/1994 |
| JP | 8 57043 A | 3/1996 |
| JP | 9 313603 A | 12/1997 |

OTHER PUBLICATIONS

English translation European Patent Application No. 0161686.*
English translation German Patent Application No. 10011208.*

* cited by examiner

METHOD FOR THE AIR BUBBLE-FREE FILING OF THE BLOOD-CONTAINING END OF A HEMODIALYZER WITH A PHYSIOLOGICAL ELECTROLYTE SOLUTION

CROSS-REFERENCE TO RELATED APPLICATION

This is a national stage of PCT/EP06/004565 filed May 15, 2006 and published in German.

BACKGROUND OF THE INVENTION

1. Field of Invention

The invention relates to a method for the air-free filling of the blood side of a hemodialysis apparatus with liquid such as a physiological electrolyte solution and for the venting of the blood side of a hemodialysis apparatus during operation.

2. Description of the Prior Art

It is already known to provide air separators formed as chambers for the separation of air in extracorporeal blood circuits in blood removing line systems, that is in the so-called venous part of the extracorporeal blood circuit. An air cushion is usually formed over a liquid level during use in these air separators since there is permanent air communication between the inside of the chamber and the environment. There are also discussions whether such a blood/air contact should be avoided for blood compatibility reasons. An air separator has therefore already been proposed in U.S. Pat. No. 5,849,065 A which is completely filled with blood. Such an air separator, however, has the disadvantage that a hydrophobic membrane which should prevent the discharge of blood is itself constantly in contact with the blood. This can now result in clogging of the membrane and furthermore the blood itself is still in contact with the air via the membrane surface since the membrane actually has a porosity of approx. 60% and thus only represents a visual air barrier. In the embodiments used, especially coated air separator membranes are used which have been developed for blood systems. These especially developed membranes are comparatively expensive. On damage to the membrane, a comparatively high safety risk results since blood can exit here, on the one hand, and since there is a risk of cross-contamination, on the other hand.

The filling of the extracorporeal blood circuit of dialysis machines is described by way of example in EP 0 560 368 A2 as well as in DE-1 00 11 208 C1.

The subsequent separation of air from a system is known from US 2003/0,135,152 A. US 2002/0017489 explains the use of a deposition line having a clamp and a check valve.

It is already known from EP 0 161 686 B1 to provide a valve and to arrange a conventional hydrophobic membrane after the valve.

SUMMARY OF THE INVENTION

It is the object of the present invention to provide a method for the air-free filling with liquid, in particular physiological electrolyte solution.

This object is solved in accordance with the invention by a simple and cost-effective method having the features described herein. For this purpose, during filling, the line system, including a chamber arranged therein, is filled with liquid, in particular physiological electrolyte solution, with a valve arranged above the chamber being opened to vent the system. The valve is closed again when the liquid has reached a hydrophobic filter arranged above the valve or the line above the valve, that is the valve is closed as soon as air is no longer located beneath the valve. After the closing of the valve, it is ensured that the total system is completely air-free and that there is also no longer any contact with the air. The interface between the filled in saline solution and the air is located outside the region separated off, that is above the valve. During subsequent operation, the blood can only be in communication with the electrolyte solution column remaining in the line. The dividing area between the blood and the electrolyte solution column can be additionally minimized on the basis of a volume minimization of the line systems. A contact of blood with a corresponding hydrophobic filter is thus avoided. The use of the more expensive hydrophobic filters which are expensive in manufacture and come into contact with blood is thereby also not necessary.

Advantageous aspects of the invention result from other features of the invention described herein.

For instance, air which has collected during operation can be displaced from the chamber by opening the valve due to, for example, inflowing blood. The corresponding air volume collecting in the chamber can be detected with the help of a level sensor and can be removed again by a brief opening of the valve. Any inflowing blood comes into contact with the previously mentioned electrolyte solution column or layer in this connection.

The complete escape of the air during the filling with the physiological electrolyte solution advantageously takes place via the measurement of the pressure development in the blood removing line system since it can be concluded on a corresponding increase in pressure that the physiological electrolyte solution contacts the membrane. The filling process with the physiological electrolyte solution can be terminated on detection of this pressure increase. The control of the venting can also be carried out via a predetermined flow control of the pump pumping into the chamber.

The invention further relates to a blood treatment apparatus for the carrying out of the method that is described herein. This blood treatment apparatus has a control unit by means of which the method can be carried out.

BRIEF DESCRIPTION OF THE DRAWINGS

Further features, details and advantages of the invention result from an embodiment which will be explained in more detail with reference to the enclosed drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
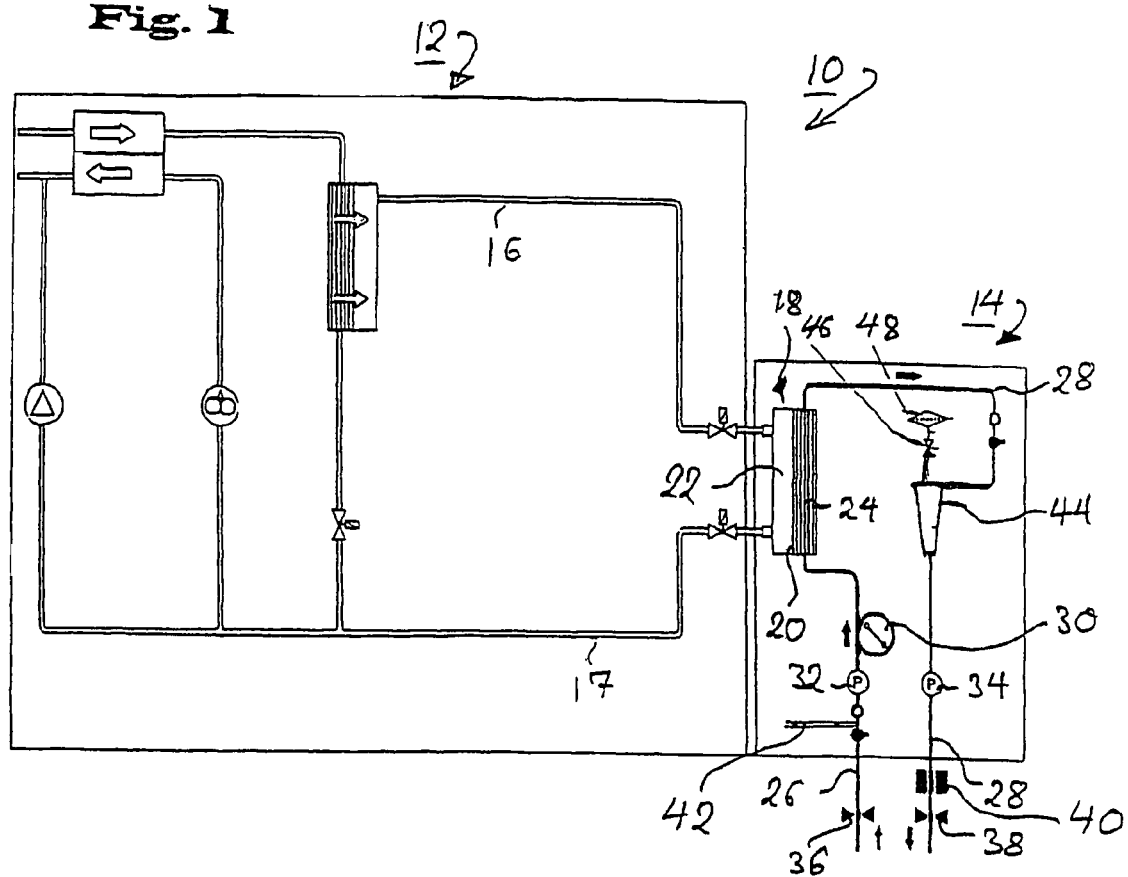
FIG. 1: a schematically illustrated embodiment of the invention.

A hemodialysis unit 10 in accordance with the invention is shown in FIG. 1. Such a unit has, in a manner known per se, a dialysis liquid circuit 12 and an extracorporeal blood circuit 14.

The dialysis liquid circuit shown here has a conventional design. The dialysis liquid moves from a dialysis liquid source not shown in any more detail via the dialysis liquid supply line 16 to the hemodialyzer 18. The hemodialyzer 18 is divided by a semi-permeable membrane 20 into a dialysis liquid chamber 22 and a blood chamber 24. The dialysis liquid chamber 22 of the hemodialyzer 18 is connected to the dialysis liquid supply line 16, on the one hand, and to the dialysis liquid removal line 17, on the other hand.

Reference can be made by way of example to the description of DE 100 11 208 A1 with respect to the further design of the dialysis liquid circuit 12 which is only shown schematically in FIG. 1. Any other design can also be selected here.

The extracorporeal blood circuit 14 has the following design. The blood chamber 24 has a supply line 26 and a removal line 28. The volume flow is adjusted by a pumping means 30. Pressure sensors 32 and 34 respectively are arranged in the respective lines 26 and 28. The supply line 26 can be pinched off via a clamp 36, whereas the removal line 28 can be pinched off by a clamp 38. A bubble detector unit 40 is additionally provided in the line 28. A connection in the supply line 26 for an anticoagulation agent infusion (e.g. heparin) is shown by 42.

Figure 2:
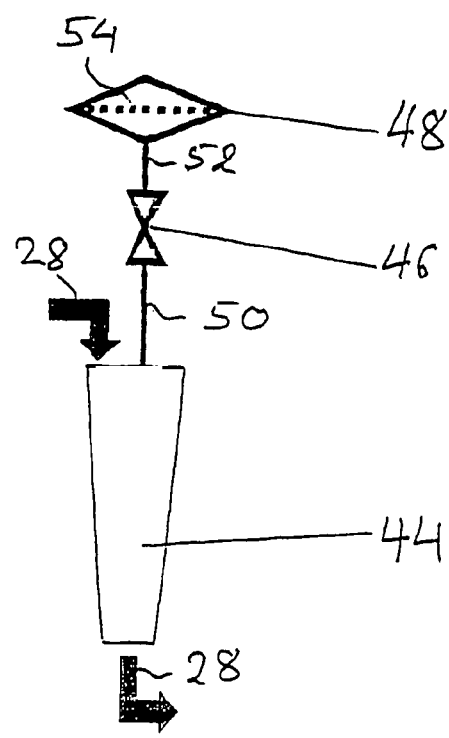
FIG. 2: a detail of the embodiment in accordance with FIG. 1.

A chamber 44 is provided in the portion of the removal line 28 arranged perpendicularly, and the removal line coming from the blood chamber 24 opens into an upper region of chamber 44 and the furthergoing portion of the removal line 28 is applied in a lower region of chamber 44. The chamber 44 fills up on operation of the hemodialysis unit 10. Ideally, the chamber is completely filled with liquid, that is with blood on operation of the hemodialysis unit. A valve 46, shown only schematically in FIG. 1, is arranged in the upper region of the chamber. A hydrophobic filter 48 is in turn provided above the valve. The more precise design of the chamber 44 with the valve 46 and the hydrophobic filter 48 results from FIG. 2. The portion of the removal line 28 opening in there as well as the removing portion of the removal line 28 in the region of the chamber 44 are shown there. As was shown in the embodiment in accordance with FIG. 2, a line, for example a tube line or a pipeline or any other passage 50, to which the valve 46 is connected, branches off from the upper portion of the chamber 44. The valve can also be arranged directly on the chamber margin. The valve 46 is in turn connected to the hydrophobic filter 48 arranged above the valve via a tube line, a pipeline or any other passage 52.

Before the hemodialysis unit 10 is put into operation, the extracorporeal blood circuit 14 is filled with a physiological electrolyte solution, as a rule a physiological saline solution. Only subsequently is the patient connected and the corresponding blood pumped through the extracorporeal blood circuit by means of the pump means 30. In this connection, the physiological electrolyte solution is displaced by the inflowing blood.

In accordance with the present invention, during filling, the blood-removing line system 28, including the chamber 44, is filled with physiological electrolyte solution for the air-free filling of the blood side of the hemodialysis unit 10, with the valve 46 remaining open until the physiological electrolyte solution has moved up to the membrane 54 of the hydrophobic filter 48 or has at least reached the line above the valve. The valve 46 is subsequently closed so that there is a physiological solution in the region above the chamber 44, namely in the communication passage 50 or 52. If the valve 46 should be arranged directly at the chamber margin, the physiological saline solution remains at least in the communication passage 52.

At the start of dialysis, the physiological electrolyte solution is displaced from the lines 26 of the blood chamber 24, from the line 28 and from the chamber 44. If air should now collect in the upper chamber region 44 during dialysis, which can be detected by a filling level measurement in the chamber 44 now shown in any detail here, the valve 46 can be opened for venting so that the air can escape through the line 50 or 52 via the hydrophobic filter 48. In this case, blood can possibly flow into the line 50, with here, however, no contact taking place with the outside atmosphere, but rather only a contact via the cross-section of the line 50 with the physiological electrolyte solution in the line.

The filling process during the filling of the extracorporeal circuit 14 with physiological electrolyte solution can be controlled via the pressure sensors 32 and 34 since the system pressure increases after reaching the membrane 54 in the hydrophobic filter 48. The initially open valve 46 is closed when this pressure increase is detected. The valve 46 can be a tube clamping valve controllable on the machine side if the line 50 or 52 is made as a tube. A cost-effective conventional hydrophobic filter can be used as the hydrophobic filter 48. Alternatively, the pump pumping into the chamber, e.g. the blood pump, can be operated such that it pumps a predetermined volume of liquid into the chamber so that air is no longer located beneath the valve.

In the embodiment in which the outflow of the chamber 44 to the valve 46 represents a dead and small branch in the closed position, the invention additionally makes use of the fact that the branch is completely filled with saline solution due to capillary forces and thus neither clots nor results in air contact.

Even a leaking or missing membrane does not result in a safety risk in the apparatus in accordance with the invention since at best saline solution can enter into the environment during filling. However, this will also become noticeable on an automatic filling by the machine in that no pressure increase is detected in the chamber during the filling process.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method for air-free filling of a blood side of a hemodialysis apparatus with a liquid, comprising
   filling a blood-conducting line system, including a chamber arranged therein, with the liquid, while opening a valve arranged above the chamber so as to vent the chamber, and
   closing the valve when the liquid has reached a hydrophobic filter arranged above the valve or a line above the valve, so that air is no longer located beneath the valve.

2. The method in accordance with claim 1, wherein the air collected during operation is displaced from the chamber by opening the valve due to inflowing blood for the venting of the hemodialysis apparatus during operation.

3. The method in accordance with claim 1, wherein complete escape of the air during the filling is determined by measuring pressure development in the blood-conducting line system or in a dialysis liquid circuit in fluid communication therewith.

4. The method in accordance with claim 1, wherein complete escape of the air during the filling is effected by measuring a filling level in the line above the valve.

5. The method in accordance with claim 1, wherein complete escape of the air is effected by detecting a filling level with a level sensor coupled to the chamber at a position beneath the valve, and a subsequent volume-controlled filling of a residual volume of the chamber with a pump that pumps into the chamber.

6. The method in accordance with claim 5, wherein the pump is a blood pump of the hemodialysis apparatus.

7. The method in accordance with claim 1, wherein the filling of the circuit is terminated by detecting a desired filling level in the line system to be filled, and a pump used for the filling continues to pump for a pre-defined time dependent on a delivery rate.

8. The method in accordance with claim 1, wherein a filling level of the chamber is monitored during operation.

9. The method in accordance with claim 5, wherein, when an air collection is determined during operation, the valve is opened until the complete escape of the air has been reached as determined by a filling level indicator above the valve, by measuring the pressure development or of a volume-controlled filling of the chamber by the pump that pumps into the chamber.

10. A blood treatment apparatus that provides for air-free filling of a blood side of a hemodialysis apparatus with a liquid, comprising
an extracorporeal blood circuit and a chamber arranged therein, including a passage branching off above the chamber with a hydrophobic filter and a valve arranged in the passage, and a conveying unit of the liquid in the extracorporeal blood circuit, and
a control unit configured to fill the extracorporeal blood circuit with the liquid by operation of the conveying unit, the valve closing in dependence on measured values of a sensor that detects a filling level in the passage or in accordance with a predetermined volume-controlled filling of the chamber to achieve a filling level of the liquid in the passage between the valve and a membrane in the hydrophobic filter.

11. The blood treatment apparatus in accordance with claim 10, wherein the sensor is a pressure sensor that detects a pressure in the chamber or a pressure in a fluid system in communication with the chamber.

12. The blood treatment apparatus in accordance with claim 10, wherein the sensor is a level sensor disposed at a line between the valve and the hydrophobic filter membrane.

13. The blood treatment apparatus in accordance with claim 10, wherein a sensor detects any desired filling level in a line system to be filled for the volume-controlled filling, and the control unit operates the conveying unit after detection of the filling level with a predetermined time that is dependent on the pumping rate.

14. The blood treatment apparatus in accordance with claim 13, wherein the sensor is a level sensor coupled to the chamber.

15. The blood treatment apparatus in accordance with claim 10, wherein the control unit displaces the air collected during operation for the venting of the hemodialysis apparatus based on inflowing blood from the chamber by opening the valve.

16. The blood treatment apparatus in accordance with claim 10, further comprising a valve in a line of the extracorporeal blood circuit leading away from the chamber, the valve being closed by the control unit during the filling or venting process.

17. The method according to claim 1, wherein the liquid is a physiological saline solution.

18. The apparatus according to claim 10, wherein the liquid is a physiological saline solution.

* * * * *